United States Patent
Zhu et al.

(10) Patent No.: US 11,049,255 B2
(45) Date of Patent: Jun. 29, 2021

(54) IMAGE PROCESSING DEVICE AND METHOD THEREOF

(71) Applicant: Hitachi, Ltd., Tokyo (JP)

(72) Inventors: Peifei Zhu, Tokyo (JP); Zisheng Li, Tokyo (JP)

(73) Assignee: HITACHI, LTD., Tokyo (JP)

( * ) Notice: Subject to any disclaimer, the term of this patent is extended or adjusted under 35 U.S.C. 154(b) by 87 days.

(21) Appl. No.: 16/327,017

(22) PCT Filed: Apr. 26, 2017

(86) PCT No.: PCT/JP2017/016556
§ 371 (c)(1),
(2) Date: Feb. 21, 2019

(87) PCT Pub. No.: WO2018/061279
PCT Pub. Date: Apr. 5, 2018

(65) Prior Publication Data
US 2019/0188858 A1    Jun. 20, 2019

(30) Foreign Application Priority Data
Sep. 29, 2016    (JP) .............................. JP2016-191093

(51) Int. Cl.
*G06T 7/149*    (2017.01)
*G06T 7/13*    (2017.01)
(Continued)

(52) U.S. Cl.
CPC .............. *G06T 7/149* (2017.01); *A61B 8/466* (2013.01); *A61B 8/483* (2013.01); *A61B 8/5207* (2013.01);
(Continued)

(58) Field of Classification Search
CPC ....... A61B 8/483; A61B 8/5207; A61B 8/466; A61B 8/5223; A61B 8/0883; G06T 7/149;
(Continued)

(56) References Cited

U.S. PATENT DOCUMENTS

| | | | | |
|---|---|---|---|---|
| 5,889,524 A | * | 3/1999 | Sheehan | ................. G06T 17/20 345/419 |
| 2001/0024517 A1 | * | 9/2001 | Labelle | ............... G06F 16/5838 382/170 |

(Continued)

FOREIGN PATENT DOCUMENTS

| JP | 2005-169120 A | 6/2005 |
|---|---|---|
| JP | 2007-312971 A | 12/2007 |
| WO | 2006/068271 A1 | 6/2006 |

OTHER PUBLICATIONS

International Search Report of PCT/JP2017/016556 dated Jun. 20, 2017.

*Primary Examiner* — Brenda C Bernardi
(74) *Attorney, Agent, or Firm* — Mattingly & Malur, PC

(57) ABSTRACT

Volume data is used for extracting a contour of a measurement object and measurement information describing anatomical structure useful for diagnosis is acquired from the contour. When volume data of a subject is inputted (S301), an image processing device detects feature points in the volume data (S302); detects contours of a plurality of parts in the volume data based on the detected feature points and anatomical definitions (S303); and optimizes boundary lines defining contours of parts contacting each other, out of the detected plural parts, so as to combine together the optimized contours of the plural parts for creating a contour of the measurement object (S304). Measurements are taken on diagnostic items useful for diagnosis based on the created contour (S305); and the acquired measurement information (Continued)

is outputted as measurement results (S306) which are displayed at a display.

8 Claims, 10 Drawing Sheets

(51) Int. Cl.
| | | |
|---|---|---|
| *G06T 7/50* | (2017.01) | |
| *G06F 3/0484* | (2013.01) | |
| *G06F 3/0486* | (2013.01) | |
| *A61B 8/08* | (2006.01) | |
| *A61B 8/00* | (2006.01) | |
| *G16H 30/20* | (2018.01) | |

(52) U.S. Cl.
CPC .......... *A61B 8/5223* (2013.01); *G06F 3/0486* (2013.01); *G06F 3/04845* (2013.01); *G06F 3/04847* (2013.01); *G06T 7/13* (2017.01); *G06T 7/50* (2017.01); *A61B 8/0883* (2013.01); *G06T 2207/10132* (2013.01); *G06T 2207/20092* (2013.01); *G06T 2207/20124* (2013.01); *G06T 2207/30048* (2013.01); *G16H 30/20* (2018.01)

(58) Field of Classification Search
CPC .......... G06T 7/0012; G06T 7/12; G06T 7/13; G06T 7/50; G06T 2207/10132; G06T 2207/20076; G06T 2207/10136; G06T 2207/30048; G06T 2207/20081; G06T 2207/20092; G06T 2207/20124; G16H 50/50; G16H 30/40; G16H 30/20; G06F 3/04845; G06F 3/04847; G06F 3/0486
See application file for complete search history.

(56) References Cited

U.S. PATENT DOCUMENTS

| | | | |
|---|---|---|---|
| 2005/0148852 A1 | 7/2005 | Tank | |
| 2008/0085043 A1 | 4/2008 | Watanabe et al. | |
| 2009/0077497 A1* | 3/2009 | Cho | G06F 3/04817 |
| | | | 715/814 |
| 2012/0281895 A1* | 11/2012 | Chono | A61B 8/5215 |
| | | | 382/128 |
| 2013/0261447 A1* | 10/2013 | Tashiro | A61B 8/5223 |
| | | | 600/437 |
| 2015/0070523 A1* | 3/2015 | Chao | H04N 5/23293 |
| | | | 348/218.1 |
| 2015/0371420 A1* | 12/2015 | Yerushalmy | G06T 3/4038 |
| | | | 382/284 |
| 2016/0086049 A1* | 3/2016 | Yamada | G06T 7/0012 |
| | | | 382/128 |

* cited by examiner

IMAGE PROCESSING DEVICE AND METHOD THEREOF

TECHNICAL FIELD

The present invention relates to an image processing device and more particularly, to an image processing technique that acquires measurement information for diagnostic use by extracting a contour of a measurement object from three-dimensional information.

BACKGROUND ART

Ultrasonic systems such as ultrasonic diagnostic equipment have a characteristic of enabling the observation of the inside of a subject without destroying the subject. Particularly in the medical field, the ultrasonic systems negate the need for surgical operations such as laparotomy for treatment of human body and hence, have found wide ranging applications as means for providing safe observation of internal organs. The heart is one of the subjects of the ultrasonic systems. With the advent of the aging society, the recent years have seen the increase in the number of people suffering cardiac valvular diseases such as mitral regurgitation. Valvuloplasty, valve-sparing surgery and the like have been widely performed as a method of treatment of the cardiac valvular diseases. For the sake of achieving success in the surgery, an exact diagnosis of the disease based on echocardiographic examination must be done before surgery.

In a conventional practice, an examiner as a user acquires as follows measurement information pieces, such as annulus diameter, valve height and valvular area, which are necessary for making a diagnosis. Namely, the examiner captures two-dimensional echocardiographic images and manually extracts a contour of the cardiac valve while watching the cross-sectional images. Unfortunately, the manual operations of extracting the cardiac valve contour and taking measurements of various diagnostic items involve complicated processes and take much time. It is also difficult to clarify a complicated three-dimensional structure such as of the cardiac valve by using the two-dimensional sectional images. More recently, a system has been provided which uses a special ultrasonic probe for acquiring volume data or three-dimensional information such as stereoscopic ultrasonic image of heart. The system automatically acquires measurement information for diagnosis from the volume data.

Patent Literature 1 is cited as an example of the related prior art documents. The technique of Patent Literature 1 is for acquisition of clinically required information such as annulus area, height and the like of the cardiac mitral valve. For acquisition of a three-dimensional image of the cardiac valve, a three-dimensional echocardiography image is generated from a two-dimensional echocardiography images obtained by scanning with an echocardiographic machine. Namely, the patent literature relates to a method of automatically extracting the three-dimensional cardiac valve image through computer processing, where the three-dimensional cardiac valve image providing for the measurement of clinically required data is automatically extracted by optimizing a fitting evaluation function (potential energy) of an annulus model in a fitting model considering the physical shapes of the heart and the annulus by means of a replica exchange method/expansion slow cooling method.

CITATION LIST

Patent Literature

PTL 1: International Publication No. WO2006/068271

SUMMARY OF INVENTION

Technical Problem

According to Patent Literature 1, the contour of the cardiac valve as regarded as one shape is extracted from the volume data. However, the object of measurement such as the cardiac valve has such a complicated shape that it is never easy to extract the whole contour of the subject at one stroke and with a high degree of precisions. It is reported that the cardiac valve includes therein a plurality of parts based on anatomical definitions, every one of which is useful for diagnosis of disease. It is therefore necessary to extract not only the whole contour of the measurement object but also boundary lines between the parts which define an internal structure. However, Patent Literature 1 does not disclose a method for extracting the boundary lines between the parts of the measurement object.

Accordingly, it is an object of the invention to provide an image processing device capable of extracting the contour of the measurement object with high precisions and measurement information necessary for diagnosis of the measurement object as well as a method thereof, which address the above-described problem.

Solution to Problem

According to an aspect of the invention for achieving the above object, an image processing device including a processor has an arrangement wherein the processor detects feature points in volume data of a measurement object; extracts contours of a plurality of parts of the measurement object based on the detected feature points and anatomical definitions; optimizes the contours of parts contacting each other, out of the extracted contours of the plural parts, so as to combine together the plural parts for creating a contour of the measurement object; and acquires measurement information therefrom.

According to another aspect of the invention for achieving the above object, an image processing method of an image processing device has an arrangement wherein the image processing device detects feature points in volume data of a measurement object; extracts contours of a plurality of parts of the measurement object based on the detected feature points and anatomical definitions; optimizes the contours of parts contacting each other, out of the extracted contours of the plural parts, so as to combine together the plural parts for creating a contour of the measurement object; and acquires measurement information therefrom.

Advantageous Effects of Invention

According to the invention, the high-precision contour and measurement information of the measurement object can be acquired.

DESCRIPTION OF EMBODIMENTS

Figure 1:
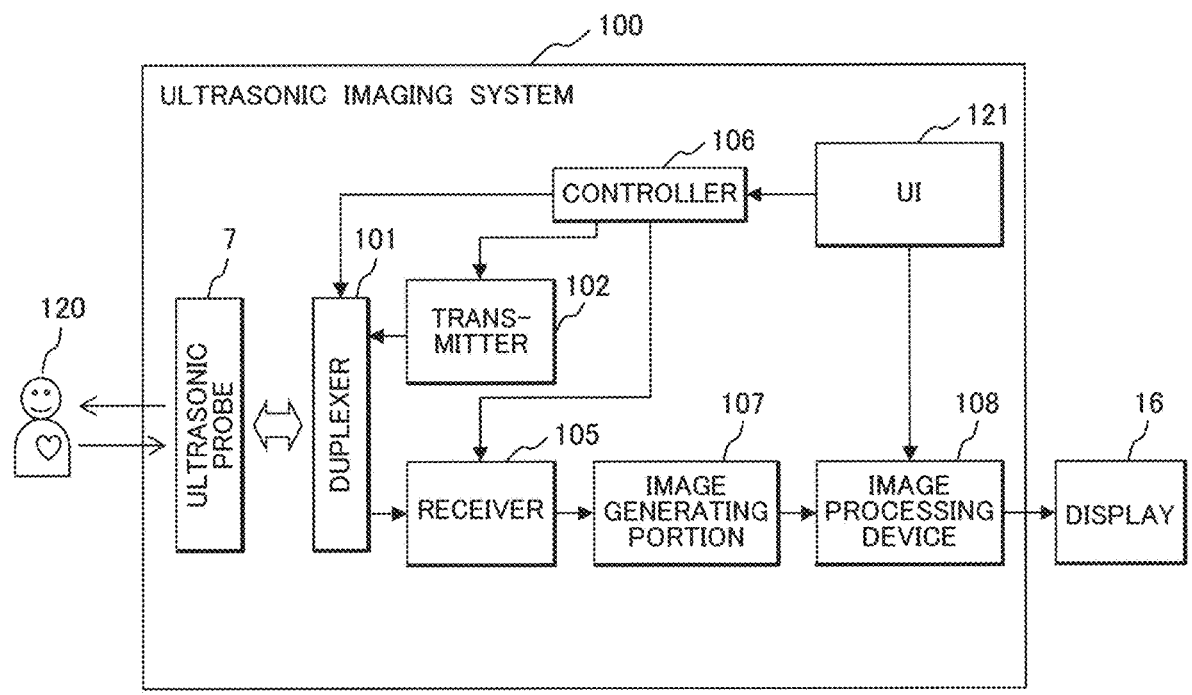
FIG. 1 is a block diagram showing an example of the whole structure of an ultrasonic imaging system according to Example 1 of the invention.

A variety of examples of the invention will be specifically described as below with reference to the accompanying drawings. Throughout the figures illustrating the examples hereof, equal or similar reference numerals are principally assigned to equal or similar components, which are explained only once in most cases to avoid repetitions. It is noted that feature points and a plurality of parts in the subject are defined to mean artificially set positions or regions of a subject organ such as heart, which are regarded as being anatomically meaningful. Out of the contours of the plural parts in the subject, a contour of a portion where the parts contact each other is referred to as a boundary line.

Example 1

Example 1 illustrates an image processing device of an ultrasonic imaging system. The image processing device has a configuration where a processor acquires measurement information by taking the steps of: detecting feature points of a measurement object which are contained in volume data acquired by transmitting/receiving an ultrasonic wave; extracting contours of plural parts of the measurement object based on the detected feature points and anatomical definitions; and optimizing the contours of the parts contacting each other (out of the detected contours of the plural parts) and combining together the plural parts so as to create a contour of the measurement object. Further, the example illustrates an image processing method of the image processing device. In this method, the image processing device acquires the measurement information by: detecting the feature points in the volume data of the measurement object; extracting the contours of the plural parts of the measurement object based on the detected feature points and the anatomical definitions; and optimizing the contours of the parts contacting each other (out of the detected contours of the plural parts) and combining together the plural parts so as to create the contour of the measurement object.

As shown in FIG. 1, for example, the ultrasonic imaging system of Example 1 includes: an ultrasonic probe 7, an image generating portion 107, and an image processing device 108. The ultrasonic probe 7 transmits the ultrasonic wave to a subject 120 via a duplexer 101 and receives an ultrasonic wave from the subject 120. The image generating portion 107 generates an ultrasonic image from a signal received from the ultrasonic probe 7. The image processing device 108 receives ultrasonic volume data from the image generating portion 107 so as to process the received data as three-dimensional information of the subject. The exemplary whole structure of the ultrasonic imaging system shown in FIG. 1 is shared by other examples.

<System Configuration and Operations>

A detailed description is made as below on a specific configuration of the ultrasonic imaging system of the example. In addition to the ultrasonic probe 7, the image generating portion 107 and the image processing device 108 as shown in FIG. 1, the ultrasonic imaging system of the example further includes: a transmitter 102, the duplexer 101, a receiver 105, a user interface (UI) 121 and a controller 106. Further, the ultrasonic imaging system is connected with a display 16 as an image display portion.

The transmitter 102 generates a transmission signal under control of the controller 106 and delivers the signal to each of the plural ultrasonic elements constituting the ultrasonic probe 7. This triggers the plural ultrasonic elements of the ultrasonic probe 7 to transmit ultrasonic waves to the subject 120, respectively. The ultrasonic waves reflected by the subject 120 go back to the plural ultrasonic elements of the ultrasonic probe 7 where the ultrasonic waves are converted to electric signals. The signals received by the ultrasonic elements are transmitted to the receiver 105 via the duplexer 101 while the receiver 105 delays the signals by predetermined delay amounts corresponding to reception focus points and adds the delayed signals. That is, the signals are phase-regulated and added. Such signal transmission and reception are repeated for each of the plural reception focus points. The phased and added signal is delivered to the image generating portion 107. The duplexer 101 selectively connects the transmitter 102 or the receiver 105 to the ultrasonic probe 7.

The image generating portion 107 generates an ultrasonic image as the volume data by performing processing for receiving the phased and added signals from the receiver 105 and arranging the received signals at positions corresponding to the reception focus points. The image processing device 108 receives the volume data from the image generating portion 107 and extracts standard sections. It is noted here that the standard section is defined to mean a sectional image complying with guidelines for standard section acquisition. Although FIG. 1 shows the display 16 located outside the system, the display 16 may also be included in the user interface 121 of the ultrasonic imaging system 100, as shown in FIG. 2.

Figure 2:
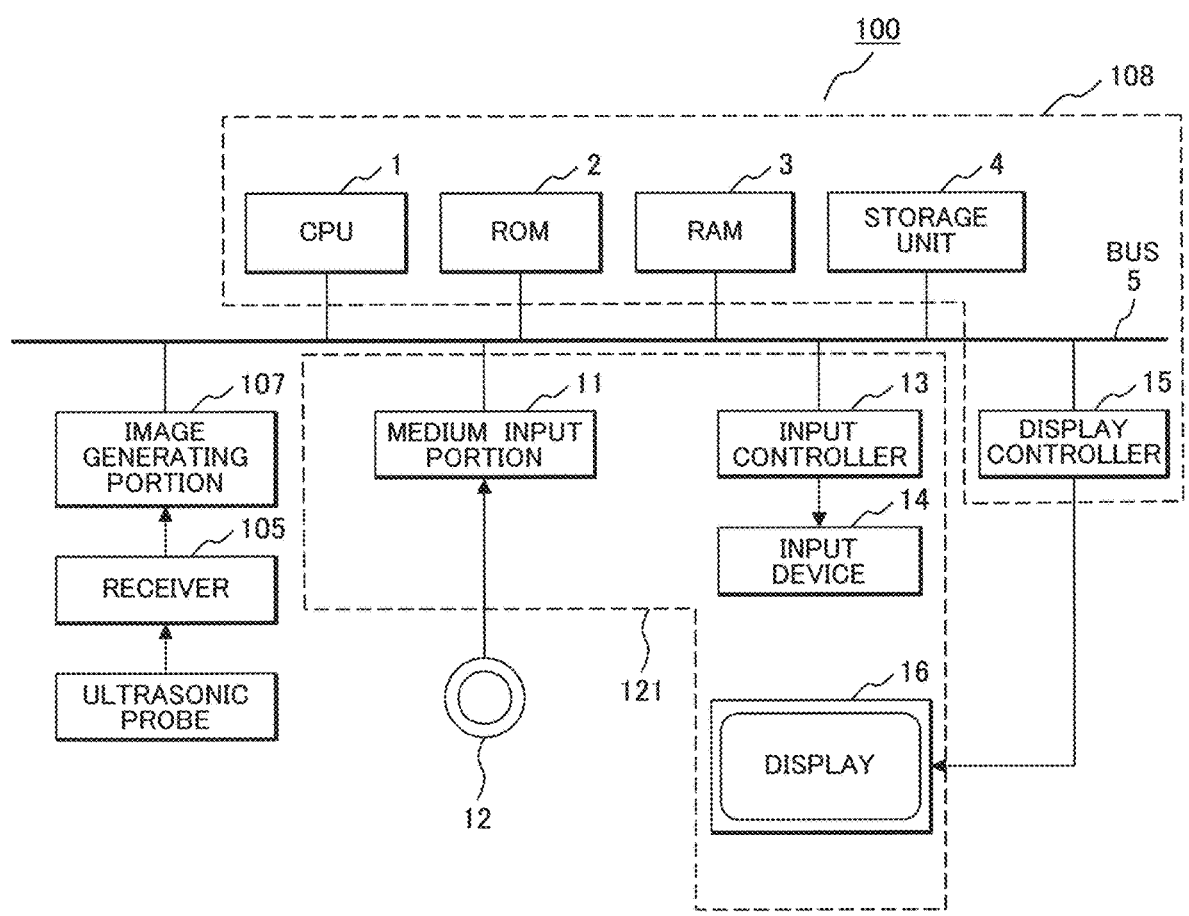
FIG. 2 is a block diagram showing an example of a hardware configuration of the ultrasonic imaging system according to Example 1 hereof.

Referring to an exemplary hardware configuration of the image processing device 108 and the user interface 121 shown in FIG. 2, a detailed description is made on the configuration and operations of the image processing device 108 and user interface 121. Similarly to FIG. 1, the exemplary hardware configuration shown in FIG. 2 is shared by the other examples to be described hereinafter.

As shown in FIG. 2, the image processing device 108 includes: a central processing unit (CPU) 1, a read only memory (ROM) 2, a random access memory (RAM) 3, a storage unit 4, and a display controller 15. The user interface 121 includes: a medium input portion 11, an input controller 13, an input device 14 and the display 16. The medium input portion 11, the input controller 13, the display controller 15 and the image generating portion 107 are interconnected by means of a data bus 5 of the image processing device 108. The display controller 15 is connected to the display 16 for control of display on the display 16. For example, the controller controllably drives the display 16 to display image data such as the standard section obtained by processing by the CPU 1.

At least one of the ROM2 and the RAMS is previously stored with an arithmetic processing program for the CPU1 and a variety of data pieces which are considered as necessary for implementation of the operations of the image processing device 108. The various processes of the image processing device 108, which will be described hereinafter, are implemented by the CPU1 executing the previously stored program in at least one of the ROM2 and the RAM3. Incidentally, the programs executed by the CPU1 may be previously stored in a storage medium 12 such as an optical disk such that the medium input portion 11 such as an optical disk drive may read the program into the RAM3.

Further, the storage unit 4 may be previously stored with the program such that the program in the storage unit 4 may be loaded into the RAM3. Otherwise, the ROM2 may be previously stored with the program. The storage unit 4 includes an unillustrated shape model database. The shape model database includes average shapes of plural parts of a test object such as cardiac valve of the subject, shape parameters of a principal component and the like as information on the contours of anatomical parts to be described hereinafter. The contour of the object is extracted by fitting the average shape in the database and the shapes of the principal components in the image.

The input device 14 of the user interface 121 is for receiving a user operation and includes, for example, a keyboard, trackball, operation panel, foot switch and the like. The input controller 13 receives an operation instruction inputted by a user via the input device 14. The operation instruction received by the input controller 13 is processed and executed by the CPU1.

Figure 3:
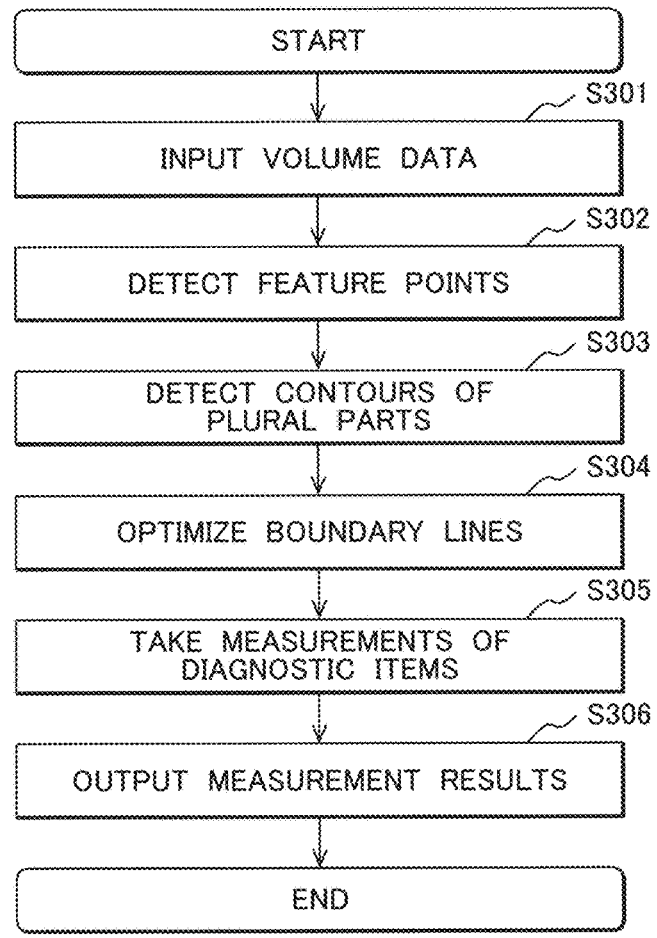
FIG. 3 is a flow chart showing an example of a processing flow of measurement of cardiac valve according to Example 1 hereof.

Next, the operations of the image processing device 108 of the example are described with reference to a flow chart of FIG. 3 showing the whole processing flow of taking measurements of cardiac valve. The processing of the flow chart can be implemented by the CPU1 executing the above-described programs.

First in Step 301 (hereinafter, written as S301), ultrasonic volume data generated by the image generating portion 107 is inputted.

In S302, feature points are detected from the inputted volume data. As will be described with reference to FIG. 4, the feature point means a position artificially set on an object organ of the subject, as considered as anatomically meaningful. The position abounds in information on characteristic quantity present on a medical image and is helpful in diagnosis. A machine learning technique based on positional information of the image characteristic quantity and the feature point to be described hereinafter is applied to the detection of the feature point.

Figure 5:
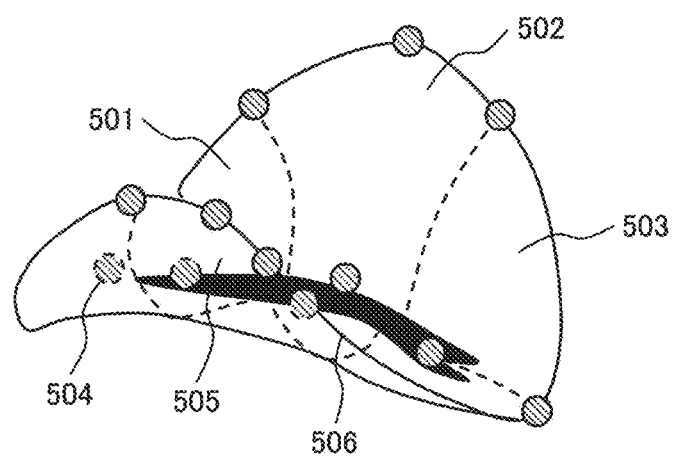
FIG. 5 is a schematic diagram showing an example of creating contours of plural parts from a cardiac mitral valve according to Example 1 hereof.
Figure 5:
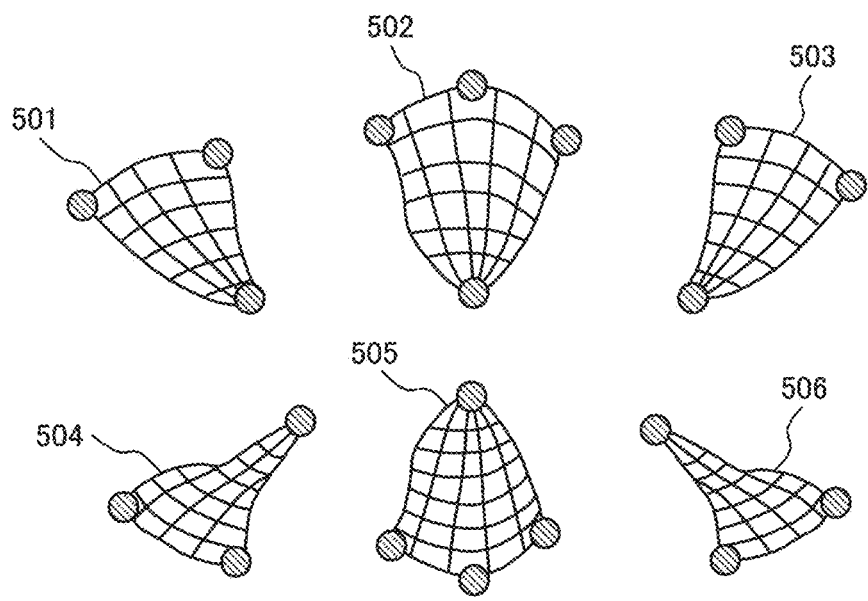

In S303, the object organ is divided into plural parts based on the anatomical definitions and a contour of the respective parts is detected. In a case where the object organ is a cardiac mitral valve, for example, the plural parts are six anatomical parts including lateral margin of anterior cusp, a lateral margin of posterior cusp and the like, as shown in FIG. 5 to be described hereinafter. Each of the parts is useful in diagnosis. A method based on a shape model, for example, is known as a contour extraction method. The shape model is a whole series of vertices constituting an outline of an organ present on the medical image. As will be described with reference to FIG. 6, the shape model includes a profile model describing how an image feature value appears around a vertex, and a shape model describing shape variations.

Constructed profile models and shape models are previously stored in the shape model database in the storage unit 4. These models are retrieved such that the shape model is fitted in an image of an inputted unknown volume data using the feature point detected in S302 as an initial position. Next, the positions of the vertices are optimized based on the restriction in the image feature value by the profile model and the restriction in the shape by the shape model. The shape of the anatomical part can be extracted by repeating this process till all the vertices reach stable positions.

In S302, the contours of the parts that contact each other, out of the plurality of parts, namely the boundary lines are optimized. As will be described hereinafter with reference to FIG. 7 and an expression 1, an optimum boundary line is created by optimizing both of information on a distance from an unoptimized contour of the part to a created boundary line and information on deviation between the created boundary line and the average shape stored in the storage unit 4. The contours of the plural parts are defined by this optimization. The contour of the whole organ can be constructed from the resultant contours of the plural parts.

In S305, measurements of the diagnostic items useful for the diagnosis such as annulus diameter, valve height, and valvular area are taken based on the created overall contour.

In S306, the CPU1 of the image processing device 108 outputs the contours of the parts extracted in S303 (part contour extraction), the whole contour reconstructed by the boundary line optimization in S304, and the measurement information of the annulus diameter, valve height, valvular area and the like as measured in S305, while the display controller 15 transmits the outputs to the display 16 which displays the outputs.

Figure 4:
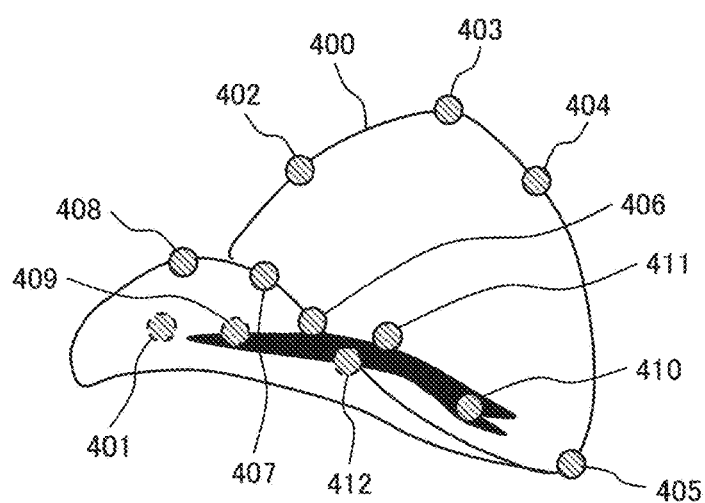
FIG. 4 is a schematic diagram showing an example of feature point setting according to Example 1 hereof.

Next, a detailed description is made on the feature point detection in Step 302 of the example with reference to FIG. 4. FIG. 4 is a schematic diagram showing an example of feature point setting in the case of cardiac mitral valve. As indicated by round stamps in FIG. 4, positions replete with feature information, such as a central part 401 of left annulus on an annular ring of mitral valve 400, an A1A2 joint 402, a central part 403 of anterior cusp of valve ring, an A2A3 joint 404, a central part 405 of right annular ring, a P1P2 joint 408, a left valve joint 409, a right valve joint 410, an anterior valve cusp 411, and a posterior valve cusp 412, are set as the feature points. The feature point is set so as to roughly determine the initial shape and position of each anatomical part.

Methods such as Hugh Forest and Support Vector Machine (SVM) are used for detection of the feature point. In a case where Hugh Forest is used, a decision tree is prepared for making decisions on details about direction and distance between various particular regions in the volume data such that a feature classifier capable of acquiring the direction and distance between arbitrary feature points from unknown volume data the same way can be generated by combining a plurality of the decision trees. That is, when unknown volume data is inputted in the feature classifier, vector information to the optimum retrieval feature point can be finally found by sequentially passing decision trees where the direction and the positional relation of the inputted region image match with those of an object region.

Next, a detailed description is made on Step 303 of extraction of the contours of plural parts according to the example. FIG. 5 shows an example of defining the plural parts of the cardiac mitral valve based on the anatomical definitions. As indicated by the dotted lines in FIG. 5, the cardiac mitral valve is divided into six parts including: a lateral margin of anterior cusp 501, a middle part of anterior cusp 502, an interior part of anterior cusp 503, a lateral margin of posterior cusp 504, a middle part of posterior cusp 505, and an interior part of posterior cusp 506. Respective shape model databases for the plural parts are previously generated and stored in the storage unit 4. The shape models are retrieved for the inputted unknown volume data so as to extract the contours of the respective parts.

Figure 6:
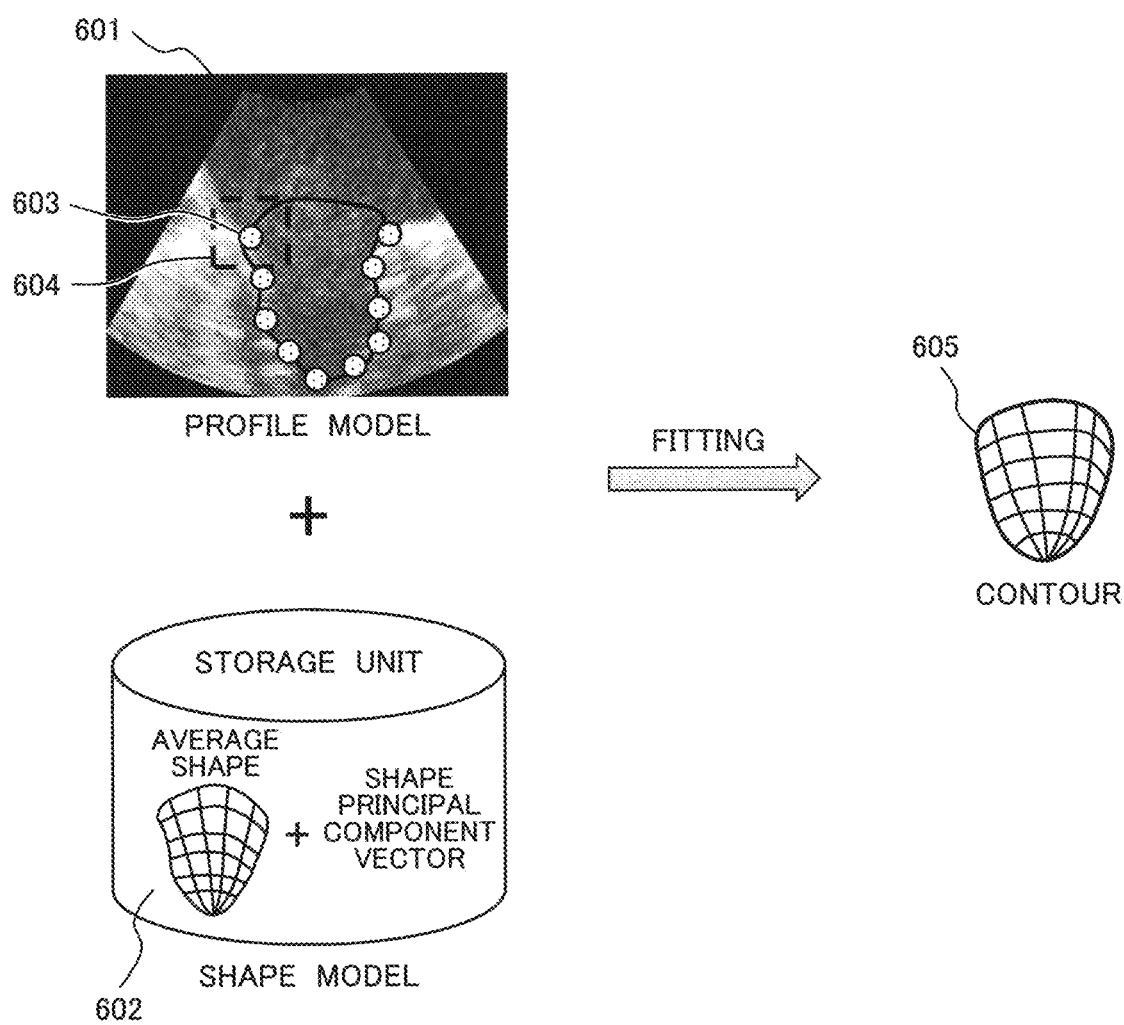
FIG. 6 is a schematic diagram showing an example of extracting a contour of a part according to Example 1 hereof.

A method based on well-known Active Shape Model (ASM) is used for contour extraction. The shape model is a whole series of vertices constituting an outline of an organ present on the medical image. FIG. 6 is a diagram showing an example of contour model construction and contour extraction in a case where the ASM method is used. The model consists of two parts. One part is a profile model 601 describing how the image feature value appears at the periphery of a vertex, while the other part is a shape model 602 describing the shape variations.

The profile model 601 is for extraction of the image feature value based on a method such as edge detection. The image feature value is extracted from a local region 604 of a vertex 603 defining the outline. The shape model 602 is constructed using Principal Component Analysis (PCA). The shape model 602 includes an average shape and a shape principal component vector representing a variation type. The average shape can be determined by calculating the average of all the shapes and construed as a feature that all the mitral valves have in common. The variation type is determined by subtracting the average shape from each of all shapes, representing how much each shape varies from the average shape. Hence, the shape of a particular region is generated by choosing some variation types as bases and adding the average shape to the combination of these base values.

The contour extraction from the constructed profile model 601 and shape model 602 is performed as follows. The feature points detected in Step 302 as represented by the hatched circles on the parts 501 to 506 in FIG. 5 are applied to the inputted unknown volume data for determination of initial contour of the part. Next, the feature value of the vertex constituting the outline is calculated based on the profile model 601. A matching score of the profile model stored in the storage unit 4 that matches this feature value is calculated. Next, a curve function including the vertex of the outline is fitted to a position of a high matching score. Then, a new vertex position is obtained by optimizing the curve function based on the shape restriction. The part contour 605 can be extracted by repeating this processing till all the points reach the stable points.

It is noted that in place of the above-described ASM method, well known Active Appearance Model method, Constrained Local Model (CLM) method or the like may also be applied to the shape extraction of the particular region.

Figure 7:
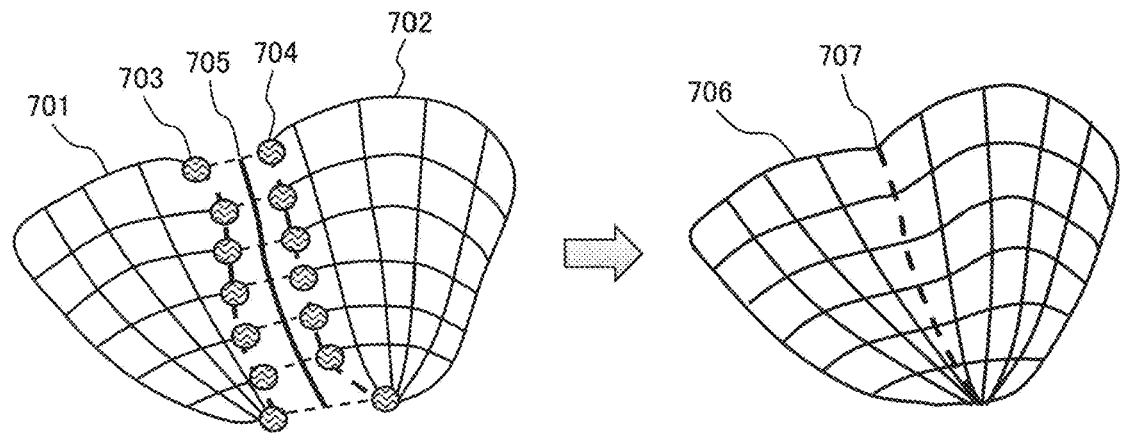
FIG. 7 is a schematic diagram showing an example of boundary line optimization according to Example 1 hereof.

Now referring to FIG. 7, the description is made on an operation in the boundary line optimizing step 304 of the example shown in FIG. 3, or the operation of optimizing boundary lines defining the contours of parts contacting each other, out of the plural parts extracted in Step 303. Since a part 701 and a part 702 contacting each other are extracted respectively, boundary lines 703 and 704 defining the contours of the contacting parts include portions not conforming to each other. This requires the modification of the boundary lines by optimization in order that a contour of the whole body is generated from the contours of the plural parts. A boundary line optimization method of the example expresses a minimization function ø(x) by using the following expression 1, for example.

$$\varphi(X) = \varepsilon_1 \Sigma_{i=1}^{n}(P_i X_i + Q_i X_i) + \varepsilon_2 \Sigma_{i=1}^{n} |X_i - \overline{S}_i| \quad \text{[Expression 1]}$$

It is noted here that $X=(X_1, X_2, \ldots X_n)$ denotes a boundary line 705 defining a contour of a portion where the parts contact each other; $X_i$ denotes the i-th vertex on the boundary line 705; $P_i$ denotes the i-th vertex on the boundary line 703 of the part 701; $Q_i$ denotes the i-th vertex on the boundary line 704 of the part 702; $P_i X_i$ denotes a distance between the vertex $P_i$ and the vertex $X_i$; $Q_i X_i$ denotes a distance between the vertex $Q_i$ and the vertex $X_i$; S with bar above denotes an average shape of a boundary line contacting the part 701 and the part 702, the average shape stored in the storage unit; and 81, 82 denote weighting factors of distance information and deviation from the average shape.

The first half of the expression 1 denotes information about distances from the boundary line 705 to the boundary line 703 and to the boundary line 704. The latter half of the expression 1 denotes shape information indicating deviations of the boundary line 705 and the average shape stored by the storage unit 4. In this expression 1, the boundary line 705 is updated by minimizing both the distance information in the first half of the expression and the shape information in the latter half of the expression. An optimum boundary line 707 can be obtained by repeating the processing till the function ø(x) reaches a value equal to a threshold value or less. Namely, out of the extracted contours of the plural parts, a processor of the image processing device 108 optimizes the boundary lines defining the contours of the parts contacting each other based on the distance information and shape information of the contours of the parts contacting each other. A contour 706 of the whole measurement object including the plural parts can be created by combining together the contours of the plural parts obtained by optimizing the boundary lines.

Figure 8:
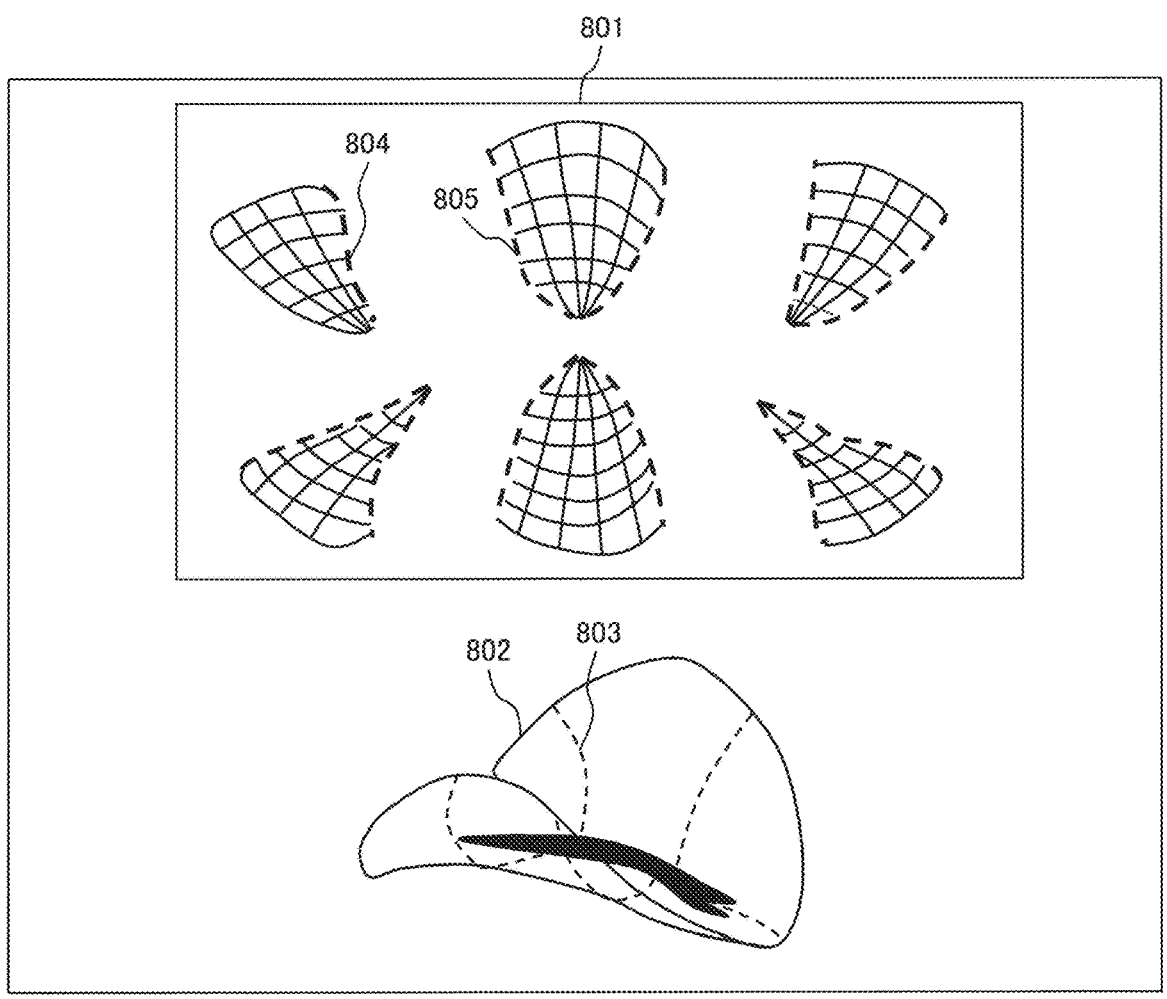
FIG. 8 is a schematic diagram showing an example of display of boundary line modification according to Example 1 hereof.

FIG. 8 shows an example where the boundary lines defining the contours of the parts contacting each other are modified by the boundary line optimization S304 and displayed on the display 16 in the device configuration of the example. The contours 801 of the plural parts detected in S303 are displayed on a display screen. A whole contour 802 is constructed from the contours 801 of the plural parts by the boundary line optimization in S304. When, of the whole contour 802, a boundary line 803 defining a contour of the parts that contact each other is modified by the optimization in S304, a boundary line 804 and a boundary line 805 of corresponding part contours are also modified and displayed concurrently. Thus, the modifying motion can be displayed on the display 16. After the boundary line optimization in S304, if it is determined that the boundary line needs correction, the user can correct the boundary line by manually dragging and dropping the boundary line with a mouse of the input device 14. Further, if the boundary line 804 is manually corrected, the image processing device 108 is adapted to perform processing for correcting the corresponding boundary line 805 as well as the boundary line 803 in the whole contour in conjunction with this correction and displays the results on the screen.

As just described, the processor of the image processing device according to the example displays the extracted contours of the plural parts and the whole contour of the measurement object on the display as the image display portion. Out of the extracted contours of the plural parts, the processor also modifies the contours of the parts contacting each other by optimizing the boundary lines defining the contours of the parts contacting each other and displays the modified contours on the display. Further, when correcting one of the contours of the parts contacting each other, the processor also modifies the contour of the other one of the contacting parts in conjunction with the correction, and displays the modified contours on the display.

Next, measurement is taken on the items useful for diagnosis such as annulus diameter, valve height, and valvular area based on the extracted contour. For instance, the annulus diameter means the maximum radius between two points on the valve ring, while the annulus height means a distance between the highest point and the lowest point on a valve ring spline. Based on the created contour, the maximum diameter and area of the valve ring are automatically calculated. The extracted contour and the measurement information including the measured annulus diameter, valve height, valvular area and the like are transmitted to the display 16 for display purpose. As just described, the processor of the image processing device is adapted to measure a distance between particular regions of the measurement object based on the contour of the measurement object and to indicate the measurement information as the measurement results on the display portion.

The ultrasonic imaging system of the example as described above is adapted to acquire the robust, high-precision contour and measurement information by taking the steps of: extracting, from the three-dimensional information on the subject, the contours of the plural parts based on the anatomical definitions of the measurement object; optimizing the boundary lines defining the contours of the parts contacting each other, out of the plural parts; and measuring the necessary diagnostic items from the optimum contour.

Example 2

In the image processing device of the ultrasonic imaging system of Example 1, Example 2 illustrates a configuration where if the user checking the extracted contour on the screen determines that the contour needs correction, the user can modify the contour by manual adjustment or can semi-automatically modify the contour by way of shape parameter adjustment.

Figure 9:
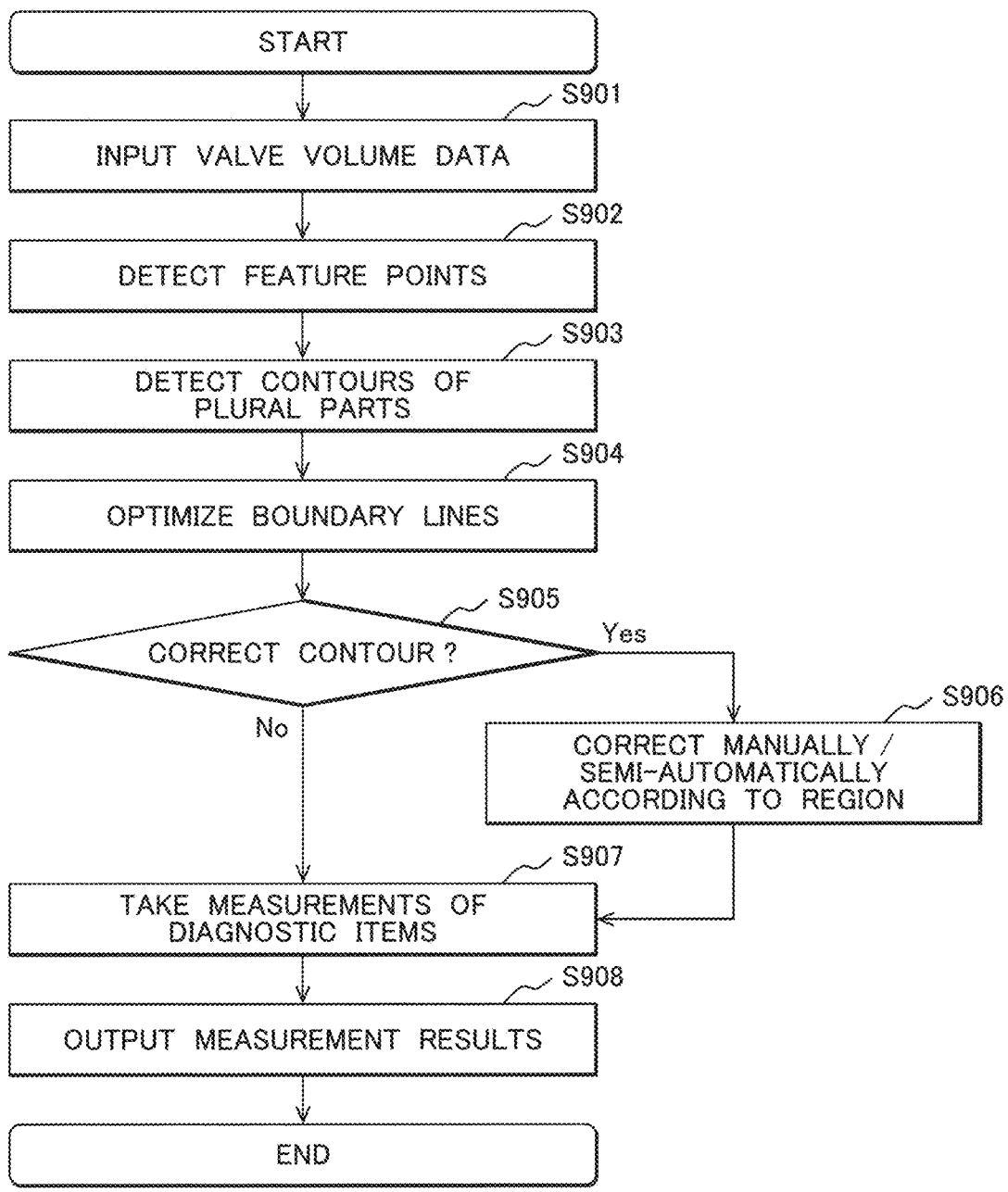
FIG. 9 is a flow chart showing an example of a processing flow of measurement of cardiac valve according to Example 2 hereof.

FIG. 9 is a flow chart showing the whole processing flow of taking cardiac valve measurements according to Example 2. In S901 to S904 of the figure, similarly to the processing flow of Example 1 shown in FIG. 3, the whole contour is constructed from the contours of the parts by taking the steps of: detecting the feature points from inputted valve volume data; detecting the contours of plural parts based on the positions of the feature points and the anatomical definitions; and optimizing the boundary lines defining the contours of the parts contacting each other out of the detected plural parts. Subsequently in S905, the user checks the contour of a part displayed on an interface screen shown in FIG. 10 which will be described hereinafter. The user determines whether or not the contour needs correction.

If it is determined that the contour needs correction (YES), the contour is manually corrected via the interface or semi-automatically corrected by way of parameter adjustment or the like in S906 of FIG. 9. The contour obtained by the boundary line optimization in S904 is modified by this correction so that a proper contour of the measurement object can be extracted. On the other hand, if it is determined that the contour does not need correction (NO), the operation flow proceeds to the measurement of diagnostic items S907. The items are measured based on the contour corrected in S906 or on the contour determined to need no correction. In S908, the measurement results are outputted to the display 16 which can display the measurement results.

Figure 10:
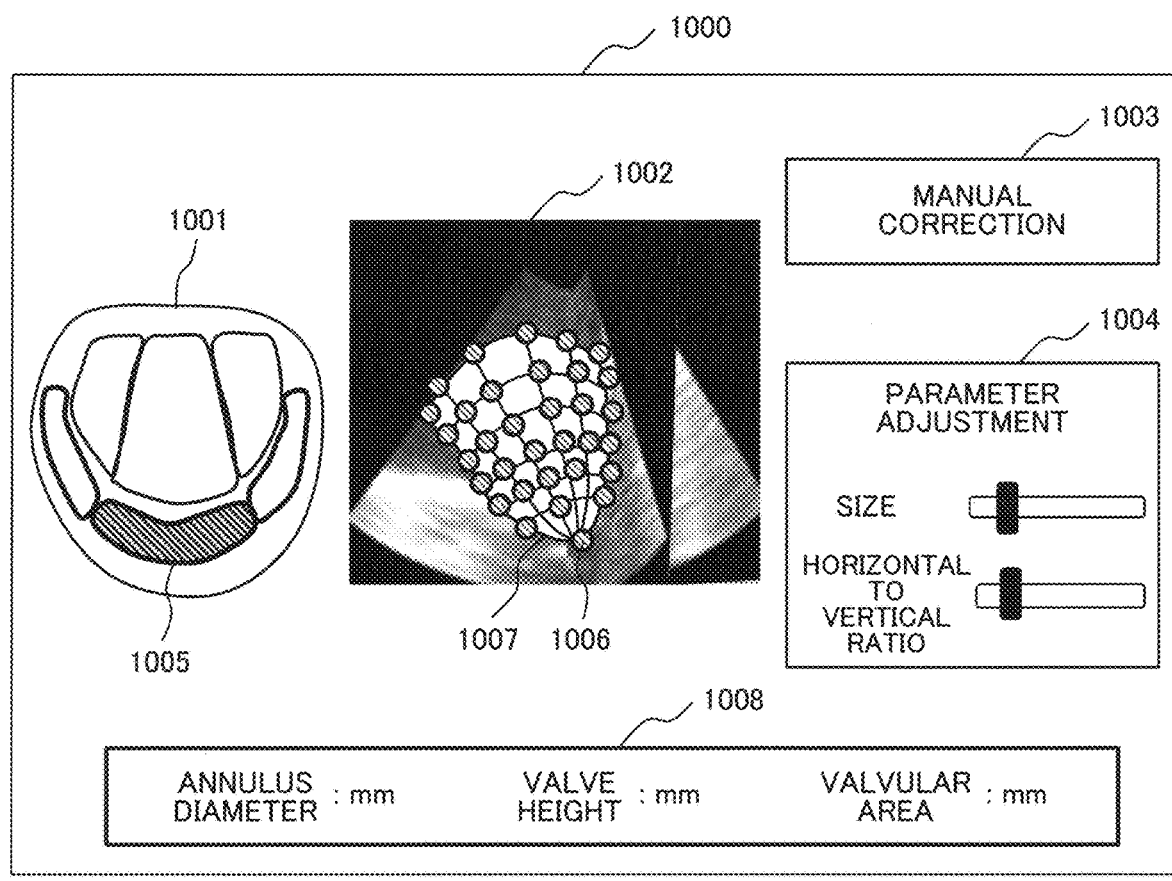
FIG. 10 is a diagram showing an example of contour modification by manual correction or shape parameter adjustment according to Example 2 hereof.

FIG. 10 shows an example of an interface for manual correction and semi-automatic correction by way of parameter adjustment, the interface displayed on the display 16 as the image display portion according to the example. An interface 1000 includes: a part selection button 1001 for selecting a part to be displayed; a display region 1002 for displaying a contour of an extracted part on a screen; a manual correction button 1003; a shape parameter adjustment control bar 1004 used for semi-automatic correction; and a measurement value display region 1008. When the part selection button 1001 is selected, a selected part is highlighted just like a part selection button 1005.

The user can check a numerical value of a shape which is extracted and displayed at the measurement value display region 1008. If the shape needs correction, the user can manually make a fine adjustment of the shape. Specifically, when the user presses down the manual correction button 1003, a previously stored manual correction program becomes executable on the CPU 1. The user consents to modification by dragging and dropping a desired region 1006 of a particular regional shape 1007 displayed in the image display region 1002 so that the user can manually correct a local contour of an area around the related region. Further, the whole shape can be adjusted by way of parameter adjustment. The user can semi-automatically accomplish scaling, rotation, shape modification and the like of a corresponding mitral valve by manipulating the control bar 1004. Next, the size, area and the like of a region to be observed is calculated from the corrected contour 1002. These calculated values are redisplayed at the measurement value display region 1008 on the screen of the interface 1000.

As just described, the image processing device of the example includes the input portion such as the interface 1000 while the processor modifies the contours of the plural parts in response to a command to correct the contours of the plural parts inputted from the input portion. The processor of the image processing device displays the parameter adjustment control bar in the image display portion and modifies the contours of the plural parts in response to the correction command by way of adjustment of the control bar. Further, the processor of the image processing device modifies the desired region in conjunction with the drag and drop of the desired region of the contours of the plural parts shown at the display portion.

According to the example, more accurate contour can be extracted to support the measurement of the diagnostic items because the user checks the extracted contour on the screen and if the contour needs correction, the user can correct the contour manually or semi-automatically by way of adjustment of the shape parameters.

Example 3

In the image processing device of the ultrasonic imaging system according to Examples 1 and 2, Example 3 illustrates a configuration where a contour of two or more adjoining organs, such as the mitral valve and aortic valve, is wholly extracted so as to provide measurement information useful for diagnosis.

Figure 11:
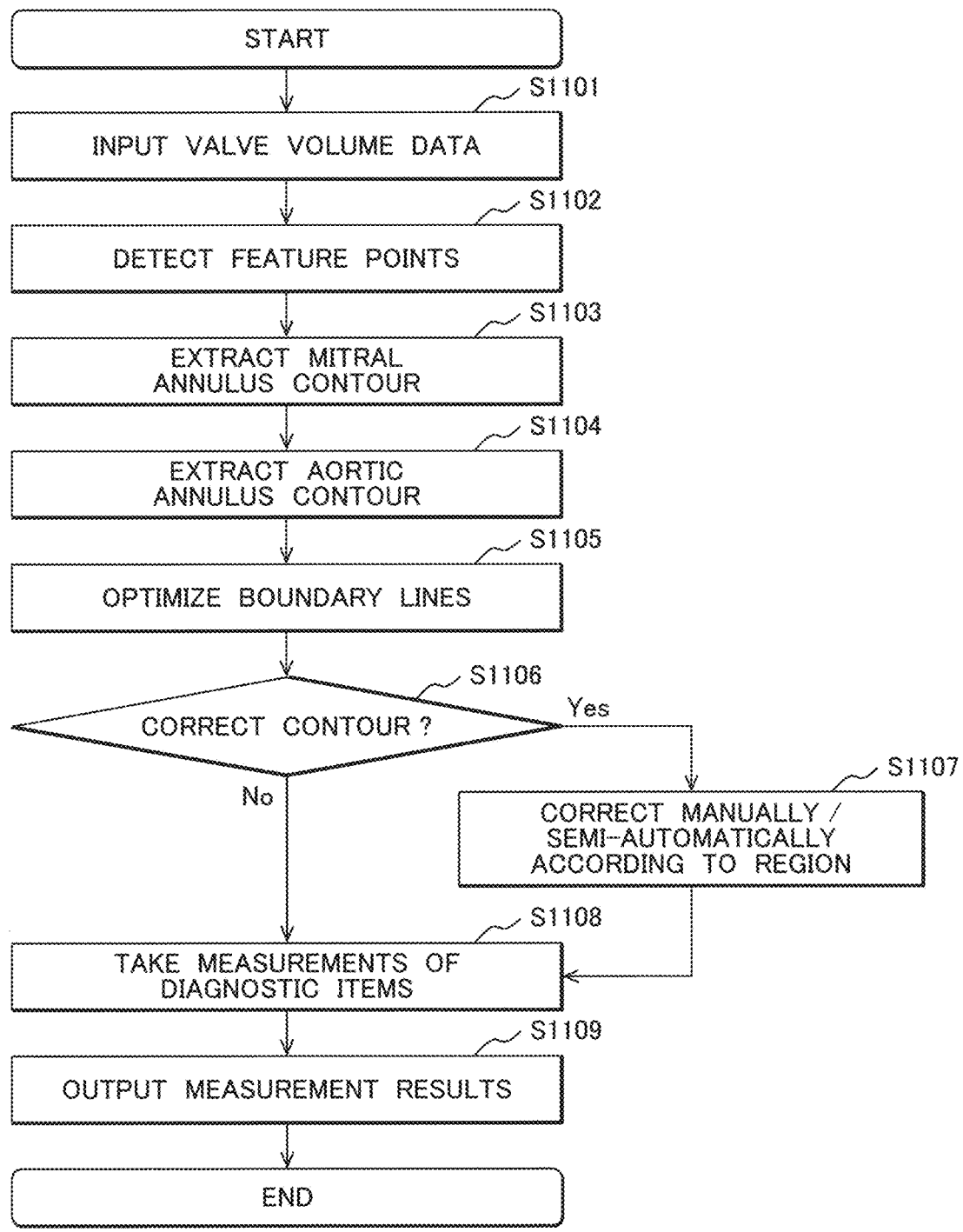
FIG. 11 is a flow chart showing an example of a processing flow of extraction of cardiac mitral valve and aortic valve according to Example 3 hereof.

FIG. 11 is a flow chart showing an example of a processing flow of extraction of cardiac mitral valve and aortic valve. In S1101, volume data including the cardiac mitral valve and aortic valve is inputted. In S1102, feature points set on the mitral valve and aortic valve are detected from the inputted valve volume data. Next, in S1103, the method of Example 1 is used for dividing the mitral valve into plural parts and the contours thereof are extracted. In S1104 of aortic valve contour extraction, the aortic valve is divided into plural parts based on the anatomical definitions and the contours thereof are extracted the same way as in the method of Example 1. In S1105, boundary lines defining the contours of the parts contacting each other, out of the extracted contours of the mitral valve and aortic valve, are optimized the same way as in S304 of Example 1. The whole contour of the combination of two organs including the mitral valve and aortic valve can be created by optimizing the boundary lines. In the subsequent steps S1106 to S1109, similarly to the processing flow illustrated by the steps S905 to S908 of Example 2, the user checks the extracted contours on the screen and if the contours need correction, the contours are modified by manual adjustment and by adjustment of shape parameters. In S1107, the items are measured based on the manually/semi-automatically corrected contours or the contours determined to need no correction. In S1109 of outputting measurement results, the measurement results are transmitted to the display 16 which displays the measurement results.

Figure 12:
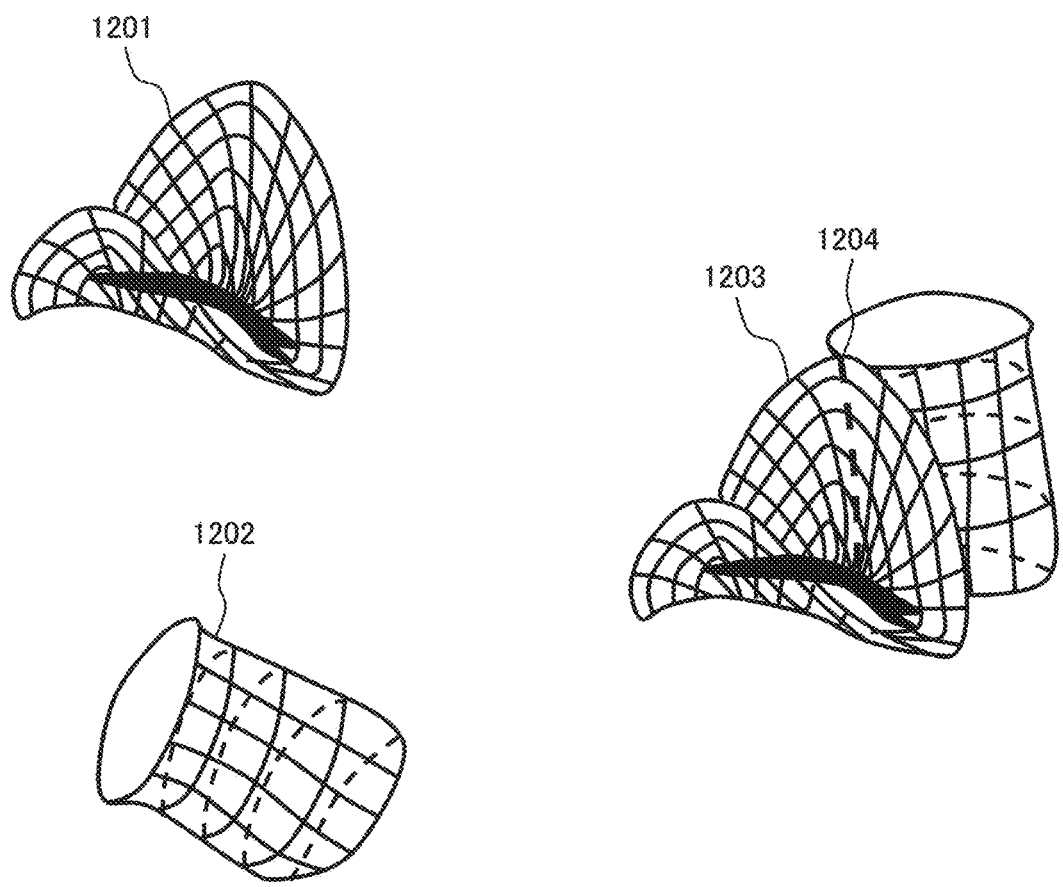
FIG. 12 is a schematic diagram showing an example of contour extraction of cardiac mitral valve and aortic valve according to Example 3 hereof.

FIG. 12 shows an example of the contour extraction of cardiac mitral valve and aortic valve according to the example. In a mitral valve contour 1201 extracted in S1103, and an aortic annulus contour 1202 extracted in S1104, a boundary line 1204 of parts contacting each other is optimized using the distance information or shape information the same way as in S304 of Example 1. A whole contour 1203 can be extracted based on the optimized contour of the two adjoining organs or the mitral valve and the aortic valve.

It is noted that the invention is not limited to the foregoing examples but includes examples corresponding to a variety of organs. The foregoing examples, for example, are the detailed illustrations to clarify the invention. The invention is not necessarily limited to what includes all the components described above. Some component of one example can be replaced by some component of another example. Further, some component of one example can be added to the arrangement of another example. A part of the arrangement of each example permits addition of some component of another example, the omission thereof or replacement thereof.

The above-described components, functions, processors and the like have been described by way of the example where a program of implementing a part or all of the components, functions, processors and the like is generated and the CPU executes the program. It goes without saying that a part or all of the components, functions, processors and the like can be implemented in a hardware by designing a part or all of the components, functions, processors and the like in an integrated circuit, for example. Namely, all or a part of the functions of the image processing device can be implemented in an integrated circuit such as ASIC (Application Specific Integrated Circuit), FPGA (Field Programmable Gate Array), and FPGA (Field Programmable Gate Array) in place of the program.

REFERENCE SIGNS LIST

1 . . . CPU,
2 . . . ROM,
3 . . . RAM,
4 . . . storage unit,
5 . . . bus,
7 . . . ultrasonic probe,
11 . . . medium input portion,
12 . . . storage medium,
13 . . . input controller,
14 . . . input device,
15 . . . display controller,
16 . . . display,
100 . . . ultrasonic imaging system,
101 . . . duplexer,
102 . . . transmitter,
105 . . . receiver,
106 . . . controller,
107 . . . image generating portion,
108 . . . image processing device,
120 . . . subject,
121 . . . user interface (UI),
601 . . . profile model,
602 . . . shape model,
701,702 . . . parts contacting each other,
703,704,804,805 . . . boundary lines defining contours of parts contacting each other,
705,803 . . . boundary line,
706,802 . . . whole contour,
707, 1204 . . . optimized boundary line,
801 . . . contours of plural parts,
1000 . . . interface,
1001, 1005 . . . part selection button,
1002 . . . image display region,
1003 . . . manual correction button,
1004 . . . control bar,
1006 . . . region,
1007 . . . shape of particular region,
1008 . . . measurement value display region,
1201 . . . mitral valve contour,
1202 . . . aortic annulus contour,

The invention claimed is:

1. An image processing device, comprising:
a processor;
a display coupled to the processor; and
a memory coupled to the processor storing instructions that when executed by the processor, cause the processor to:
detect feature points in volume data of a measurement object;
extract contours of a plurality of parts of the measurement object based on the detected feature points and anatomical definitions;
optimize the contours of parts contacting each other, out of the extracted contours of the plural parts, to combine the plural parts to create a contour of the measurement object; and
acquire measurements of diagnostic items of anatomical structure from the optimized contours; and
create boundary lines between the contours of the parts contacting each other,
wherein out of the extracted contours of the parts, the processor modifies the contours of the parts contacting each other by optimizing the boundary lines between the contours of the parts contacting each other; and displays the modified contours on the display, wherein the processor displays the extracted contours of the plural parts and the contour of the measurement object on the display, wherein the processor displays a control bar for parameter adjustment on the display and modifies the contours of the plural parts in response to an instruction for correction by adjustment of the control bar, and wherein executing the stored instructions further causes the processor to optimize the boundary lines by determining distances from the respective contours of the parts contacting each other to the boundary line between the respective contours of the parts contacting each other and minimizing the distances, and determining deviations of the boundary line with respect to shape model information of the contours of the parts contacting each other and minimizing the deviations.

2. The image processing device according to claim 1, wherein the processor modifies one of the contours of the parts contacting each other, concurrently modifying the contour of the other one of the parts contacting each other; and displays the modified contours on the display.

3. The image processing device according to claim 1, wherein the processor measures a distance between particular regions of the measurement object based on the contour of the measurement object and displays the measurement results on the display.

4. The image processing device according to claim 1, further comprising an input portion,
wherein the processor modifies the contours of the plural parts in response to an instruction for correction of the contours of the plural parts as inputted from the input portion.

5. The image processing device according to claim 1, wherein in response to a drag-and-drop operation for a desired region of the contours of the plural parts displayed on the display, the processor modifies the contour of the desired region.

6. An image processing method for an image processing device that includes a processor coupled to a memory, the processor executing instructions stored in the memory comprising:

detecting feature points in volume data of a measurement object;

extracting contours of a plurality of parts of the measurement object based on the detected feature points and anatomical definitions;

optimizing the contours of parts contacting each other, out of the extracted contours of the plural parts, to combine the plural parts to create a contour of the measurement object;

acquiring measurements of diagnostic items of anatomical structure from the optimized contours; and creating boundary lines between the contours of the parts contacting each other, wherein out of the extracted contours of the parts, the processor modifies the contours of the parts contacting each other by optimizing the boundary lines between the contours of the parts contacting each other; and displays the modified contours, wherein the processor displays the extracted contours of the plural parts and the contour of the measurement object on a display, wherein the processor displays a control bar on the display for parameter adjustment and modifies the contours of the plural parts in response to an instruction for correction by adjustment of the control bar, and wherein the processor further executes instructions stored in the memory to optimize the boundary lines by determining distances from the respective contours of the parts contacting each other to the boundary line between the respective contours of the parts contacting each other and minimizing the distances, and determining deviations of the boundary line with respect to shape model information of the contours of the parts contacting each other and minimizing the deviations.

7. The image processing method according to claim 6, wherein the image processing device modifies one of the contours of the parts contacting each other, concurrently modifying the contour of the other one of the parts contacting each other and displays the modified contours.

8. The image processing method according to claim 6, wherein the image processing device measures a distance between particular regions of the measurement object based on the contour of the measurement object and displays the measurement results.

* * * * *